United States Patent [19]

Nguyen

[11] Patent Number: 5,202,102

[45] Date of Patent: Apr. 13, 1993

[54] GAS PHASE DEHYDROHALOGENATION USING A PRETREATED CATALYST

[75] Inventor: Hong A. Nguyen, Lake Jackson, Tex.

[73] Assignee: The Dow Chemical Company, Midland, Mich.

[21] Appl. No.: 703,976

[22] Filed: May 22, 1991

[51] Int. Cl.$^5$ .............................................. C01B 7/00
[52] U.S. Cl. ...................... 423/240; 423/DIG. 13; 208/262.1; 585/612; 585/641; 588/205; 570/227
[58] Field of Search .............. 423/240, 659, DIG. 13, 423/DIG. 20; 208/262.1, 262.5; 585/359, 612, 641, 733; 588/205, 248; 570/227

[56] References Cited

U.S. PATENT DOCUMENTS

| | | | |
|---|---|---|---|
| 2,249,512 | 7/1941 | Wimmer et al. | 260/654 |
| 2,253,471 | 8/1941 | Muskat et al. | 423/79 |
| 2,410,541 | 11/1946 | Joyce | 260/654 |
| 2,593,451 | 4/1952 | Hill et al. | 260/654 |
| 2,676,997 | 4/1954 | Brown et al. | 260/654 |
| 2,803,677 | 8/1957 | Neher et al. | 260/656 |
| 2,803,678 | 8/1957 | Conrad | 260/654 |
| 3,268,602 | 8/1966 | Goble et al. | 260/654 |
| 3,304,336 | 2/1967 | Callahan | 260/654 |
| 3,553,281 | 1/1971 | Goble et al. | 260/683.68 |
| 3,567,794 | 3/1971 | Eberly | 260/650 |
| 3,637,872 | 1/1972 | Berkowitz | 260/654 D |
| 3,725,304 | 4/1973 | Wilheim | 252/441 |
| 3,760,015 | 9/1973 | Berkowitz | 260/658 R |
| 3,870,762 | 3/1975 | Stacey et al. | 260/654 D |
| 3,892,683 | 7/1975 | Germanas | 252/442 |
| 3,948,804 | 4/1976 | Rausch | 252/442 |
| 3,968,053 | 7/1976 | Rausch | 252/439 |
| 4,016,068 | 4/1977 | Rausch | 208/139 |
| 4,225,519 | 9/1980 | Reinhardt | 260/654 D |
| 4,317,800 | 3/1982 | Sloterdijk et al. | 423/1 |
| 4,485,081 | 11/1984 | Magistro | 423/481 |
| 4,672,146 | 6/1987 | Abrevaya et al. | 585/660 |
| 4,899,001 | 2/1990 | Kalnes et al. | 585/310 |
| 4,982,039 | 1/1991 | Benson et al. | 585/469 |

OTHER PUBLICATIONS

Indian J. Technol., 1978, 16(6), pp. 223–231 Jun. 1978.
Indian J. Technol., 1878(16)6, pp. 232–237 Jun. 1978.
Derwent 45405 K/19 (abstract only of J58055-436) to Nissan Chem Ind. KK Sep. 26, 1981.
Derwent 83504B/46 (abstract only of J54130-506) to Daikin Kogyo KK Mar. 30, 1978.
Derwent 12223V/07 (abstract only of J48085-51) to Kureha Chem. Ind. Co., Ltd. Feb. 22, 1972.

*Primary Examiner*—Gary P. Straub
*Assistant Examiner*—Timothy C. Vanoy

[57] ABSTRACT

A process is disclosed which comprises: contacting a catalyst such as alumina silica, aluminosilicates, titanium oxide, magnesium oxide, and the metals of Groups III and IIB of the Periodic Table under reducing conditions with a gaseous mixture comprising elemental chlorine gas and a diluent under conditions effective to improve the ability of the catalyst to dehydrohalogenate halogenated hydrocarbons: contacting the catalyst with a halogenated hydrocarbon feedstock, the halogenated hydrocarbon feedstock with or without a carrier gas, in the gas phase under dehydrohalogenation conditions; and recovering a dehydrohalogenated product.

18 Claims, No Drawings

GAS PHASE DEHYDROHALOGENATION USING A PRETREATED CATALYST

BACKGROUND OF THE INVENTION

This invention relates to gas phase dehydrohalogenation processes using pretreated catalysts.

Vinylidene chloride and related unsaturated, halogenated organic compounds are important monomers leading to many polymeric materials. In U.S. Pat. No. 2,803,677, a method is disclosed wherein 1,1,1-trichloroethane is dehydrochlorinated in the gas phase over activated alumina. The reference reports that at a temperature of 250° C., the method produces a 95.8% yield of vinylidene chloride. However, the process produces poor yields at lower temperatures and the lifetime of the catalyst is relatively short. Lower temperatures are desirable because production costs are reduced. What is needed is a process which increases the conversion rate of halogenated hydrocarbons in gas phase reactions to unsaturated compounds over alumina, preferably at low reaction temperatures. Likewise, a process which would increase the lifetime of the alumina catalyst would be desirable.

Additionally, the prior art generally lacks efficient gas phase catalytic dehydrohalogenation processes using catalysts other than alumina. The public would benefit from such processes due to the increased knowledge in this technology and due to the advantages associated with gas phase processes such as low production costs and reduced waste relative to liquid phase processes.

SUMMARY OF THE INVENTION

It has now been found that alumina which has been pretreated with a gaseous stream containing elemental chlorine gas produces unexpectedly high activity in the dehydrohalogenation of halogenated hydrocarbons, especially at low reaction temperatures. Surprisingly, the pretreated alumina exhibits long lifetime even at elevated temperatures.

Accordingly, in one respect, the present invention is a process which comprises: (A) contacting alumina under reducing conditions with a gaseous mixture comprising elemental chlorine gas and a diluent under conditions effective to improve the ability of the catalyst to dehydrohalogenate halogenated hydrocarbons; (B) contacting the alumina with a halogenated hydrocarbon feedstock, the halogenated hydrocarbon feedstock with or without a carrier gas, in the gas phase under dehydrohalogenation conditions: and (C) recovering a dehydrohalogenated product.

It has also been found that several additional catalysts are useful in dehydrohalogenation reactions after contact with a gaseous stream containing elemental chlorine gas. The treated catalysts achieve very high activity in the dehydrohalogenation of halogenated hydrocarbons. Thus, in another respect, the present invention is a process comprising: (A) contacting a catalyst under reducing conditions with a gaseous mixture comprising elemental chlorine gas and a diluent under conditions effective to improve the ability of the catalyst to dehydrohalogenate halogenated hydrocarbons, the catalyst selected from the group consisting of silica, aluminosilicates, titanium oxide, magnesium oxide, and the metals of Groups III and IIB of the Periodic Table; (B) contacting the catalyst with a halogenated hydrocarbon feedstock, the halogenated hydrocarbon feedstock with or without a carrier gas, in the gas phase under dehydrohalogenation conditions; and (C) recovering a dehydrohalogenated product.

The process of the present invention produces unexpectedly high yields at temperatures below about 275° C., particularly at about 125° C. Other advantages of the present invention include improved conversion rates, high product selectivity, and increased catalyst lifetime.

DETAILED DESCRIPTION OF ILLUSTRATIVE EMBODIMENTS

The process of the present invention is generally employed to dehydrohalogenate halogenated hydrocarbons in the gas phase over certain catalysts.

Suitable halogenated hydrocarbon feedstock useful in the present invention comprises one or more halogenated hydrocarbons having between 2 and 6 carbon atoms and one or more halogen atoms. Preferably, the halogenated hydrocarbon comprises one or more chlorinated hydrocarbons having between 2 and 6 carbon atoms and one or more chlorine atoms. More preferably halogenated hydrocarbon feedstock comprises one or more chlorinated ethanes such as 1,1,2-trichloroethane, 1,1,1-trichloroethane, 1,1-dichloroethane and 1,2-dichloroethane. Most preferably, the halogenated hydrocarbon feedstock comprises 1,1,1-trichloroethane.

The catalysts which are useful in the present invention include alumina, silica, mixed aluminosilicates, titanium oxide, magnesium oxide, the metals of Group III of the periodic table such as aluminum, and the metals of Group IIB of the Periodic Table such as zinc. All forms of alumina are useful in the present invention. Preferred catalysts are alumina, zinc, aluminum, and titanium oxide. While it has been found that several catalysts are useful in the present invention, one catalyst has been found to be particularly useful as a dehydrohalogenation catalyst and, consequently, the most preferred catalyst is a gamma alumina having a macroporous structure. The gamma alumina has a surface area of from about 10 $m^2/g$ to 500 $m^2/g$, preferably from about 100 $m^2/g$ to 350 $m^2/g$, and a macropore volume of from about 10% to 50% of the total available pore volume, preferably from about 15% to 40%. A macropore, as used herein, is a pore having a diameter of at least 100 angstroms.

Before pretreating the desired catalyst with a chlorine mixture, the catalyst is preferably heated to a temperature of 200° C. to 350° C. in a stream of an inert gas, such as nitrogen, to remove moisture from the catalyst. This step insures that the catalyst is free of surface air and moisture which would otherwise deleteriously effect the following pretreatment step.

Next, in the pretreatment step, the catalyst is treated under reducing conditions with a gaseous mixture comprising elemental chlorine gas and a diluent. The concentration of chlorine in the gaseous mixture may be any concentration effective to pretreat the catalyst so long as the concentration of chlorine is not so high as to cause runaway chlorination of the catalyst. The time needed to pretreat the catalyst will vary depending on concentration of chlorine in the gaseous mixture, amount of catalyst to be pretreated, and temperature. In practice, the concentration of chlorine in the gaseous mixture will be maximized, depending on the variables, to minimize the time for the pretreatment. It is preferred to run the pretreatment step under reducing conditions essentially free of oxidizing gases such as air, oxygen, and the like. The most preferred diluent is hydrogen chloride.

A preferred gaseous mixture used to treat the catalyst comprises 0.1 to 20 percent chlorine in diluent, most preferably between 0.5 and 15 percent chlorine in diluent. The pretreatment step can be carried out at any temperature effective to render the surface of the catalyst more active in a subsequent dehydrohalogenation reaction. Preferably, the pretreatment step is carried out at a temperature between about 75° C. and 500° C., more preferably between 100° C. and 300° C. The gas hourly space velocity of the gaseous mixture over the catalyst is between about 100 hr$^{-1}$ and 3000 hr$^{-1}$ for between about 0.1 and 10 hours, most preferably between about 500 hr$^{-1}$ and 2000 hr$^{-1}$ for between about 0.5 and 5 hours. The pretreatment should produce a catalyst having less than 1 percent chlorine by weight. The pressure may be sub-atmospheric, atmospheric, or super-atmospheric.

The subsequent dehydrohalogenation step is carried out in the gas phase. Preferably, the temperature is between about 50° C. and 500° C., more preferably between about 100° C. and 350° C. The gas hourly space velocity of the halogenated hydrocarbon feedstock over the pretreated catalyst is preferably between about 100 hr$^{-1}$ to 5000 hr$^{-1}$, more preferably between about 500 hr$^{-1}$ and 3000 hr$^{-1}$. The gas hourly space velocity of the halogenated hydrocarbon feedstock passing through the reaction zone can be controlled to obtain the necessary contact time between reactant and catalyst to promote the desired dehydrohalogenation. In general, the most advantageous contact period is dependent upon several variables such as the scale of the operation, quantity of catalyst in the reactor, and the type of reactor employed. A contact time of as high as about 20 seconds and as low as about 0.1 seconds is suitable for the present invention. Typically, as contact time increases, conversion rate goes up while selectivity goes down.

A carrier gas may be employed as a component of the halogenated hydrocarbon feedstock during the dehydrohalogenation step. The carrier gas can be any gas which is inert in the dehydrohalogenation step. Non-limiting examples of carrier gases useful in the present invention are nitrogen, helium, and hydrogen chloride. When a carrier gas is employed, the mole percentage of carrier gas in the halogenated hydrocarbon feedstock can be from about 1 to 99, preferably from about 80 to 95.

During the dehydrohalogenation step, the pressure may be sub-atmospheric, atmospheric, or super-atmospheric. Preferably, the pressure is between about 0 and 200 psig, more preferably between about 0 and 100 psig.

The dehydrohalogenation and pretreatment steps can be carried out in conventional fixed bed, fluid bed, or riser type reactors and can utilize any desired temperature controlling means, either internal or external. In addition, the dehydrohalogenation and pretreatment steps may be carried out as a batch, semicontinuous, or continuous processes. When desired the catalyst can be regenerated using methods known to those skilled in the art such as by heating the catalyst in air at elevated temperatures to burn off surface buildup.

The dehydrohalogenated product of the present invention may be recovered and further purified by methods known generally to those skilled in the art.

SPECIFIC EMBODIMENTS OF THE INVENTION

The following examples are given to illustrate the invention and should not be construed as limiting its scope. All parts and percentages are by weight unless otherwise indicated.

EXAMPLE 1

A lab reactor consisting of a ⅜" diameter stainless steel tube 20" long is packed with 10 cubic centimeter ("cc") of a gamma alumina having a surface area from 100 m$^2$/g to 350 m$^2$/g and a macropore volume of 15% to 40% of the total available pore volume. The alumina is heated for about 2 hours at about 250°–300° C. in a nitrogen stream. Next, the catalyst is pretreated by passing a stream of 5% chlorine in hydrogen chloride over the alumina at 275° C. for 4 hours. Following pretreatment, a feedstock comprising 22 cc/minute of 1,1,1-trichloroethane vapor and 167 cc/minute of helium is passed over the treated alumina. The outlet from the reactor is analyzed by online gas chromatography. The results are given in the following Table I:

TABLE I

| | Temperature (°C.) | Conversion (%) | Vinylidene Chloride Selectivity (%) |
|---|---|---|---|
| Run #1 | 125 | 91.90 | 99.93 |
| Run #2 | 125 | 97.47 | 100.00 |
| Run #3 | 125 | 95.49 | 100.00 |

From Table I, it can be concluded that the pretreated alumina produces excellent results at low reaction temperatures. The average conversion is about 95% with the selectivity toward vinylidene chloride being about 100%.

EXAMPLE 2

The experiment of Example 1 is repeated except the feedstock is 167 cc/minute of gaseous 1,1,1-trichloroethane. The results are given in the following Table II.

TABLE II

| | Temperature (°C.) | Conversion (%) | Vinylidene Chloride Selectivity (%) |
|---|---|---|---|
| Run #1 | 125 | 81.46 | 100.00 |
| Run #2 | 200 | 99.14 | 100.00 |
| Run #3 | 275 | 99.50 | 100.00 |
| Run #4 | 325 | 99.53 | 100.00 |

Example 2 shows that the pretreated alumina produces excellent results at various temperature ranges.

EXAMPLE 3

A laboratory reactor consisting of a ⅜" diameter stainless steel tube 20" long is used. 10 cc of metallic zinc powder is loaded into the tube and is pretreated by passing a stream of 3% to 5% chlorine in hydrogen chloride over it for 4 hours at 275° C. A feed stream consisting of 167 cc/minute of gaseous 1,1,1-trichloroethane is then passed over the catalyst. The effluent from the reactor is analyzed by online gas chromatography. The results are given in the following Table III:

TABLE III

| Temperature (°C.) | Conversion (%) | Vinylidene Selectivity (%) |
|---|---|---|
| 125 | 0.05 | 100.00 |
| 200 | 29.10 | 100.00 |
| 275 | 55.30 | 100.00 |
| 325 | 62.73 | 99.79 |
| 375 | 94.65 | 100.00 |

EXAMPLE 4

The experiment of Example 3 is repeated except the catalyst is 10 cc of 0.75 mm diameter aluminum wire in 3-7 mm lengths and the catalyst is pretreated in a stream of 5% chlorine in hydrogen chloride at 100° C. for 30 minutes. The results are given in the following TABLE IV:

TABLE IV

| Temperature (°C.) | Conversion (%) | Vinylidene Selectivity (%) |
|---|---|---|
| 125 | 36.73 | 100.00 |
| 165 | 47.00 | 100.00 |
| 200 | 91.45 | 100.00 |

EXAMPLE 5

The procedure of Example 2 is repeated except that titanium oxide is substituted as the catalyst. At a reaction temperature of 274° C., ambient pressure, and a gas hourly space velocity of 1000 hr$^{-1}$, the conversion rate is 82.72% with a selectivity of 100% toward vinylidene chloride.

The results of Examples 3-5 show that zinc, titanium oxide, and aluminum can be used effectively in the process of the present invention.

What is claimed is:

1. A process which comprises:
   (A) contacting dry alumina under conditions essentially free of oxygen and water with a gaseous mixture comprising elemental chlorine gas and a hydrogen chloride under conditions effective to improve the ability of the catalyst to dehydrohalogenate halogenated hydrocarbons;
   (B) contacting the alumina with a halogenated hydrocarbon feedstock containing one or more chlorinated hydrocarbons selected from the group consisting of 1,1,1,-trichloroethane 1,1-dichloroethane, chloroethane, 1,2-dichloroethane, and 1,1,2-trichloroethane, the halogenated hydrocarbon feedstock with or without a carrier gas, wherein the gas hourly space velocity of the halogenated hydrocarbons feedstock is between about 100 hr$^{-1}$ and 5000 hr$^{-1}$ in the gas phase at a temperature between 50° C. and 500° C. under dehydrohalogenation conditions to produce an unsaturated, dehydrogenated product; and
   (C) recovering the unsaturated, dehydrohalogenated product.

2. The process of claim 1 wherein the gaseous mixture comprises between 0.1 and 20 percent chlorine in hydrogen chloride.

3. The process of claim 1 wherein the alumina is gamma alumina having a surface area of from about 10 m$^2$/g to 500 m$^2$/g and a macropore volume of from about 10% to 50% of the total available pore volume.

4. The process of claim 1 wherein the alumina is gamma alumina having a surface area of from about 100 m$^2$/g to 350 m$^2$/g and a macropore volume of from about 15% to 40% of the total available pore volume.

5. The process of claim 1 wherein Step A is conducted at a temperature from about 75° C. and 500° C.

6. The process of claim 1 wherein Step A is conducted at a temperature from about 100° C. and 300° C.

7. The process of claim 1 wherein Step A is carried out for between 0.1 and 24 hours.

8. The process of claim 1 wherein the gas hourly space velocity of the gaseous mixture during Step A is between about 100 hr$^{-1}$ and 5000 hr$^{-1}$ 9. The process of claim 1 wherein the temperature in Step B is between about 100° C. and 350° C.

10. The process of claim 1 wherein the chlorinated hydrocarbon is 1,1,1-trichloroethane.

11. A process which comprising:
   (A) contacting a dry catalyst under conditions essentially free of oxygen and water with a gaseous mixture comprising elemental chlorine gas and hydrogen chloride under conditions effective to improve the ability of the catalyst to dehydrohalogenate halogenated hydrocarbons; the catalyst selected from the group consisting of silica, aluminosilicates, titanium oxide, magnesium oxide, aluminum, and the metals of Group IIB of the Periodic Table;
   (B) contacting the catalyst with a halogenated hydrocarbon feedstock containing one or more chlorinated hydrocarbons selected from the group consisting of 1,1,1,-trichloroethane, 1,1-dichloroethane, chloroethane, 1,2-dichloroethane, and 1,1,2-trichloroethane, the halogenated hydrocarbon feedstock with or without a carrier gas, wherein the gas hourly spaced velocity of the halogenated hydrocarbon feedstock is between about 100 hr$^{-1}$ and 5000 hr$^{-1}$, in the gas phase at a temperature between 50° C. and 500° C. under dehydrohalogenation conditions to produce an unsaturated, dehydrogenated product; and
   (C) recovering the unsaturated, dehydrohalogenated product.

12. The process of claim 11 wherein the gaseous mixture comprises between 0.1 and 20 percent chlorine in hydrogen chloride.

13. The process of claim 11 wherein the gaseous mixture is contacted with the catalyst for between about 0.1 and 24 hours.

14. The process of claim 11 wherein Step A is conducted at a temperature from about 75° C. and 500° C.

15. The process of claim 11 wherein Step A is conducted at a temperature from about 100° C. and 300° C.

16. The process of claim 11 wherein the gaseous mixture has a gas hourly space velocity over the catalyst of between about 500 hr$^{-1}$ and 5000 hr$^{-1}$.

17. The process of claim 11 wherein the chlorinated hydrocarbon is 1,1,1-trichloroethane.

18. The process of claim 11 wherein the temperature in Step B is between about 100° C. and 350° C.

* * * * *